United States Patent
Holly et al.

(10) Patent No.: US 8,106,810 B2
(45) Date of Patent: Jan. 31, 2012

(54) MILLIMETER WAVE FILTERS

(75) Inventors: Sandor Holly, Woodland Hills, CA (US); Nicholas Koumvakalis, Thousand Oaks, CA (US); Robert A. Smith, Hampton Cove, AL (US)

(73) Assignee: The Boeing Company, Chicago, IL (US)

(*) Notice: Subject to any disclaimer, the term of this patent is extended or adjusted under 35 U.S.C. 154(b) by 99 days.

(21) Appl. No.: 12/264,128

(22) Filed: Nov. 3, 2008

(65) Prior Publication Data

US 2010/0001894 A1    Jan. 7, 2010

Related U.S. Application Data

(60) Provisional application No. 61/078,174, filed on Jul. 3, 2008.

(51) Int. Cl.
*H01Q 17/00* (2006.01)
(52) U.S. Cl. .................. 342/1; 342/5; 343/812
(58) Field of Classification Search .............. 342/1, 5; 343/812
See application file for complete search history.

(56) References Cited

U.S. PATENT DOCUMENTS

| | | | |
|---|---|---|---|
| 2,632,058 A | 11/1947 | Gray | |
| 3,348,093 A | 10/1967 | Holly | |
| 3,705,956 A | 12/1972 | Dertouzos | |
| 3,852,755 A | 12/1974 | Works et al. | |
| 3,919,638 A | 11/1975 | Belden, Jr. | |
| 4,264,814 A | 4/1981 | Freund et al. | |
| 4,600,559 A | 7/1986 | Hiatt | |
| 4,634,968 A | 1/1987 | Aslan | |
| 4,638,813 A | 1/1987 | Turner | |
| 4,806,747 A | 2/1989 | Dunavan et al. | |
| 4,942,291 A | 7/1990 | Dietrich | |
| 5,030,962 A | 7/1991 | Rees | |
| 5,103,083 A | 4/1992 | Reed et al. | |
| 5,148,182 A * | 9/1992 | Gautier et al. | 343/754 |
| 5,214,432 A * | 5/1993 | Kasevich et al. | 342/3 |
| 5,233,263 A | 8/1993 | Cronin et al. | |
| 5,308,439 A | 5/1994 | Cronin et al. | |
| 5,420,595 A | 5/1995 | Zhang et al. | |
| 5,483,060 A | 1/1996 | Sugiura et al. | |
| 5,756,999 A | 5/1998 | Parrish et al. | |
| 5,856,803 A | 1/1999 | Pevler | |
| 5,939,721 A | 8/1999 | Jacobsen et al. | |
| 6,492,957 B2 | 12/2002 | Carillo, Jr. et al. | |
| 6,605,808 B2 | 8/2003 | Michan et al. | |
| 6,864,825 B2 | 3/2005 | Holly | |

(Continued)

FOREIGN PATENT DOCUMENTS

GB   2121612 A   12/1983

(Continued)

OTHER PUBLICATIONS

U.S. Appl. No. 12/022,891, filed Jan. 30, 2008, Sandor Holly et al.

(Continued)

*Primary Examiner* — Timothy A Brainard (74) *Attorney, Agent, or Firm* — Haynes and Boone, LLP (57) ABSTRACT

An electromagnetic radiation filter uses a plurality of dipole antennas to mitigate the transmission of electromagnetic radiation. The dipole antennas can form one or more arrays that scatter electromagnetic radiation. Examples of application include mitigating the reception of a difference frequency in non-linear radar, use in protective goggles, and use in a protective shield.

11 Claims, 4 Drawing Sheets

U.S. PATENT DOCUMENTS

| | | | |
|---|---|---|---|
| 6,943,742 | B2 | 9/2005 | Holly |
| 6,944,486 | B2 | 9/2005 | Braig et al. |
| 6,950,076 | B2 | 9/2005 | Holly |
| 6,999,041 | B2 * | 2/2006 | Holly ........................ 343/820 |
| 7,009,575 | B2 | 3/2006 | Holly et al. |
| 7,122,813 | B2 | 10/2006 | Linfield et al. |
| 7,142,147 | B2 | 11/2006 | Holly |
| 7,265,331 | B2 | 9/2007 | Muenter et al. |
| 7,473,898 | B2 | 1/2009 | Holly et al. |
| 2002/0075189 | A1 | 6/2002 | Carillo, Jr. et al. |
| 2004/0008149 | A1 | 1/2004 | Killen et al. |
| 2005/0052310 | A1 * | 3/2005 | Snaper ........................... 342/1 |
| 2005/0088358 | A1 | 4/2005 | Larry et al. |
| 2005/0179611 | A1 * | 8/2005 | Holly ........................ 343/820 |
| 2006/0202123 | A1 | 9/2006 | Vuillermoz et al. |
| 2007/0085757 | A1 * | 4/2007 | Sievenpiper ................ 343/909 |
| 2007/0199365 | A1 * | 8/2007 | Skowaisa et al. ............. 73/1.35 |
| 2007/0237829 | A1 * | 10/2007 | Dadachova et al. .......... 424/489 |
| 2008/0017813 | A1 * | 1/2008 | Vetrovec et al. .......... 250/504 R |
| 2008/0291108 | A1 | 11/2008 | Holly et al. |

FOREIGN PATENT DOCUMENTS

| | | |
|---|---|---|
| JP | 01101006 | 4/1989 |
| JP | 2006-211637 | 8/2006 |
| WO | 03/019738 A1 | 3/2003 |
| WO | 2005/093904 A1 | 10/2005 |
| WO | 2006/088802 A2 | 8/2006 |

OTHER PUBLICATIONS

U.S. Appl. No. 12/264,153, filed Nov. 3, 2008, Sandor Holly et al.

U.S. Appl. No. 12/264,152, filed Nov. 3, 2008, Sandor Holly et al.

PCT/US2006/005057; Feb. 14, 2006; The Boeing Company.

PCT/US2008/061106; Apr. 22, 2008; The Boeing Company.

Maier, W.B., Freund, S. M., Holland, R.F. & Beattie, Photolytic separation of D from H. in cryogenic solutions of formaldehyde 69, 1961 (1978).

J. T. Kindt and C. A. Schmuttenmaer. Far-infrared dielectric properties of polar liquids probed by femtosecond THz pulse spectroscopy. Journal of Physical Chemistry, 100:10373-10379, 1996.

Park et al., A Novel lateral field emitter triode with Insitu vacuum encapulation, international electron devices meeting, 1996.

Park et al., Lateral field emission diodes using SIMOX wafer, IEEE transactions on electron devices, vol. 44, No. 6, Jun. 1997.

Milanovic et al., Micromachining Technology for Lateral Field Emission Devices, IEEE Transactions on Electron Devices, vol. 48, No. 1, Jan. 2001.

Peter H. Siegel, Terahertz Technology, IEEE Transactions on Microwave Theory and Techniques, Mar. 2002, pp. 910-928, vol. 50, No. 3.

Peter H. Siegel, THz Technology; An Overview, International Journal of High Speed Electronics and Systems, 2003, pp. 1-44, vol. 13, No. 2, World Scientific Publishing Company, USA.

Raman et al., A W-Band Dielectric-Lens-Based Integrated Monopulse Radar Receiver, IEEE Transactions on Microwave Theory and Techniques, Dec. 1998, pp. 2308-2316, vol. 46, No. 12.

Filipovic et al., Off-Axis Properties of Silicon and Quartez dielectric lens Antennas, IEEE Transcations on Antennas and Progapation, May 1997, pp. 760-766, vol. 45, No. 5.

* cited by examiner

MILLIMETER WAVE FILTERS

PRIORITY CLAIM

This patent application claims the benefit of the priority date of U.S. provisional patent application Ser. No. 61/078,174, filed on Jul. 3, 2008 and entitled Millimeter Wave Filters Using Two and Three Dimensional Resonant Arrays pursuant to 35 USC 119. The entire contents of this provisional patent application are hereby expressly incorporated by reference.

TECHNICAL FIELD

The present invention relates generally to antennas and, more particularly, to electromagnetic radiation filters such as millimeter wave filters using two and/or three-dimensional resonant antenna arrays.

BACKGROUND

In many laboratory and industrial settings devices are used to protect instruments and people from the detrimental effects of high-power laser radiation. Similarly, there is a need in the art for protection from the harmful effects of other types of radiation, e.g., electromagnetic radiation in the millimeter (mm) wave range. As such, it would be beneficial to provide such protection.

SUMMARY

Systems and methods are disclosed herein to provide for the filtering of electromagnetic radiation. For example, a filter can allow some frequencies of electromagnetic radiation to pass therethrough and can inhibit other frequencies of electromagnetic radiation from passing therethrough.

In accordance with an example of an embodiment, an electromagnetic radiation filter can comprise a plurality of dipole antennas that are configured to mitigate the transmission of electromagnetic radiation.

In accordance with an example of an embodiment, a method for filtering electromagnetic radiation can comprise using a plurality of dipole antennas that are configured to absorb the electromagnetic radiation and/or to re-radiate the electromagnetic radiation in a different direction.

In accordance with an example of an embodiment, an antenna for a non-linear radar system can comprise a horn and a filter. The filter can inhibit the reception of one or more frequencies of electromagnetic radiation by the horn. Thus, the filter can selectively allow some frequencies to be received by the non-linear radar system while effectively preventing other frequencies from being received thereby. The filter can comprise plurality of dipole antennas.

In accordance with an example of an embodiment, a method for selectively receiving desired electromagnetic radiation can comprise filtering the electromagnetic radiation with a plurality of dipole antennas before the electromagnetic radiation is incident upon a receive antenna (such as a receive antenna included in a non-linear radar system).

In accordance with an example of an embodiment, a non-linear radar system can comprise a transmit antenna, a receive antenna, and a filter. The transmit antenna can be configured to transmit first and second frequencies of electromagnetic radiation. The receive antenna can be configured to receive a third frequency of electromagnetic radiation. The filter can be configured to inhibit reception of the first and second frequencies of electromagnetic radiation by the receive antenna so as to prevent the first and second frequencies from adversely affecting the operation of the non-linear radar system (such as by forming undesirable intermodulation products within the non-linear radar system).

In accordance with an example of an embodiment, a method for practicing non-linear radar can comprise transmitting first and second frequencies of electromagnetic radiation and receiving a third frequency of electromagnetic radiation. Undesirable reception of the first and second frequencies of electromagnetic radiation can be inhibited.

In accordance with an example of an embodiment, goggles for protecting eyes from electromagnetic radiation can comprise a filter. The filter can comprise a plurality of dipole antennas. The dipole antennas can mitigate the transmission of undesirable electromagnetic radiation through the filter while allowing visible light to pass therethrough.

In accordance with an example of an embodiment, a method for protecting eyes from electromagnetic radiation can comprise filtering electromagnetic radiation incident upon the eyes using a plurality of dipole antennas. The dipole antennas can mitigate the transmission of electromagnetic radiation through the filter while at the same time allowing transmission of a visible light portion of the electromagnetic spectrum.

In accordance with an example of an embodiment, a shield for protection from electromagnetic radiation can comprise a filter. The filter can comprise a plurality of dipole antennas. The dipole antennas can mitigate the transmission of a selected band of electromagnetic radiation through the filter.

In accordance with an example of an embodiment, a method for providing protection from electromagnetic radiation can comprise filtering electromagnetic radiation incident upon the eyes using a plurality of dipole antennas. The dipole antennas can mitigate the transmission of electromagnetic radiation through the filter.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION

Methods and systems are disclosed for shielding instruments, electronics, sensors, human eyes, canine eyes, equine eyes, and the like from electromagnetic radiation, e.g., short wavelength electromagnetic radiation. According to an example of an embodiment, a filter can receive incident electromagnetic radiation and can re-radiate unwanted, e.g., harmful, spectral components of the electromagnetic radiation in a direction that is substantially perpendicular to the direction of the received electromagnetic radiation.

Such re-radiation can be due to scattering. The scattering can be caused by dipole antennas that are formed upon a surface of a substrate, such as a transparent window, for example.

One or more examples of embodiments can include a two-dimensional and/or a three-dimensional resonant array of dipole antennas that are configured to provide substantial attenuation in one or more frequency bands. Such attenuation can be in the millimeter and/or sub-millimeter range of frequencies, for example.

According to one or more examples of embodiments, a window can be constructed. The window can be transparent in a substantial portion, e.g., most, of the electromagnetic spectrum. For example, the window can be transparent in at least portions of the visible, infrared, microwave, and/or radio frequencies. The window can also provide substantial, e.g., high, attenuation in one or more specific bands. Such attenuation can be accomplished by scattering rather than absorption.

This property facilitates the fabrication of filters that can accommodate comparatively large incident power densities, i.e., much higher than filter whose spectral characteristics depend on absorption (rather than resonance and interference).

In applications of difference-frequency (non-linear) radar (NLR), the front-end of the non-linear radar receiver can undesirably produce its own difference frequency $\Delta f$. This occurs when the receiver picks up back-scattered, outgoing millimeter wave radiation, $f_1$ and $f_2$, (the illuminating radiation, as discussed further below).

The generation of the unwanted difference frequency $\Delta f$ is caused by nonlinear circuit components in the receiver itself. The presence of such a self-generated difference frequency $\Delta f$ within the non-linear radar receiver can undesirably affect the operation of the non-linear radar system. The self-generated difference frequency signal $\Delta f$ can interfere with or degrade the ability of the receiver to properly detect a difference frequency signal $\Delta f$ from a target.

When a non-linear radar system is used to detect the presence of non-linear electronic components contained within a remote target at a distance, then the receiver of the system is tuned to respond to the difference frequency $\Delta f$ that is generated by the target. The difference frequency $\Delta f$ is generated from the illuminating signal, $f_1$ and $f_2$, by non-linear components, non-linear structures, and/or oxidized or corroded surfaces of the target according to well-known principles.

However, in some cases, the transmitted radar signals, $f_1$ and $f_2$, from the transmitter that are directed to the target are reflected back to the receiver. In such instances, it is important to prevent these reflected radar signals, $f_1$ and $f_2$, from entering the receiver aperture. If signals at these frequencies have access to the nonlinear components of the receiver, they can produce undesirable signals at the difference frequency $\Delta f$, as discussed above. These undesirable signals can not be distinguished from the genuine $\Delta f$ return signals that are produced by the target.

According to an example of an embodiment, a filter inhibits a receiver from receiving back-reflected signals, $f_1$ and $f_2$, such as those components that may be present in the received radiation. The difference frequency $\Delta f$ produced by the target, on the other hand, can be readily transmitted through the filter and received.

There are many applications of such filters. For example, an embodiment of the filter can be incorporated into goggles. Such goggles can protect eyes, human and otherwise, from exposure to millimeter wave radiation, while at the same time providing excellent visual transparency.

It is very hard to shield instruments, electronics, sensors, and the like from short wave radiation. This is particularly true when the wavelength is just a few millimeters or shorter (such as frequencies in the 100 GHz range, W-band, and higher). Such frequencies tend to penetrate many enclosures.

According to an example of an embodiment, a filter can comprise a two dimensional array of dipoles. The dipole elements can be configured in a series of rows that are aligned substantially parallel with respect to one another. All dipole elements can be driven in phase. Other configurations are likewise possible, as discussed herein.

Figure 1:
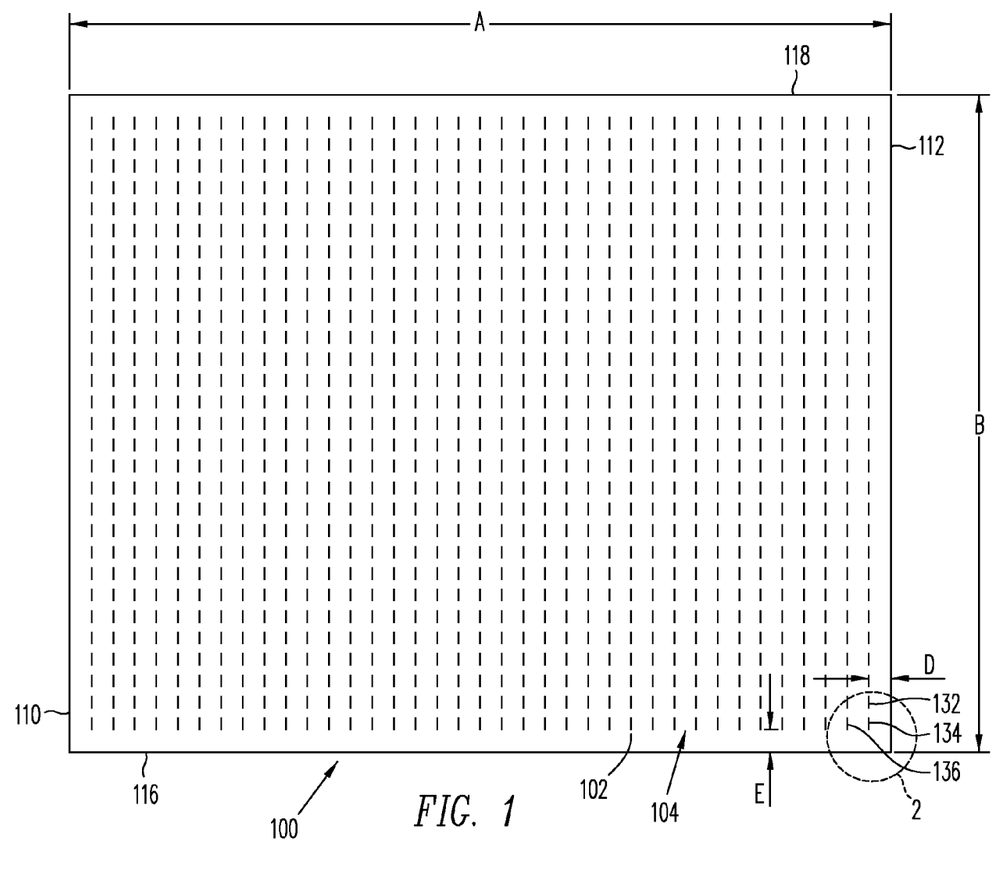
FIG. 1 is a semi-schematic diagram that shows a filter, according to an example of an embodiment.

The separation of adjacent rows of dipoles can be approximately one wavelength of a difference frequency $\Delta f$ of electromagnetic radiation that is scattered. Values for dimensions of such an array can be calculated for a particular application. Such separation can produce a radiation pattern wherein the radiation tends to be greatest in the vicinity of the plane of the dipoles. Each row of such an array can also be referred to as an "end-fire array". When a multitude of such one dimensional dipole arrays are organized in a plane, such as shown in FIG. 1, they cooperate to produce maximum radiation in the vicinity of the plane and minimum radiation in a direction perpendicular to the plane.

If a plane wave of single frequency is perpendicularly incident upon such a two-dimensional array of dipoles, with the plane wave's polarization (E field orientation) aligned with directions of the dipoles, and if the frequency of this plane wave resonates with the dipoles (the dipoles each can be ½ wavelength in length if they are suspended in a vacuum, but can be shorter if formed upon dielectric plate), then the incident radiation will scatter in the plane of the dipole array. Such scattering in the plane of the dipole array thus can provide substantial attenuation in the direction of the propagation of the wave.

Thus, the filter can attenuate single frequencies. The filter can also attenuate a pair of closely spaced frequencies for applications in non-linear radar, as discussed herein. For example, the resonant frequency of the dipoles can be between the two frequencies of the pair and the Q of each dipole can be made to be broad enough to accommodate both frequencies. In this manner, any number of frequencies can be attenuated.

According to an example of an embodiment, such dipoles can be formed upon a dielectric plate or substrate. The substrate can comprise glass or other materials that have a very low conductivity at the frequency of interest.

At frequencies in the millimeter wave portion of the spectrum, quartz and silicon have very low losses, assuming the silicon is of electronic grade. Any dielectric material (with a dielectric constant larger than one) will reduce the resonant length of a half-wave dipole. For example, silicon or quartz can be used. Silicon has a dielectric constant of 11.2 and quartz has a much lower dielectric constant of 3.8 at millimeter wavelengths.

According to an example of an embodiment, such dipoles can be produced by an evaporation technique. For example, such dipoles can be produced by the evaporation and deposition of gold. The pattern of evaporation can be controlled by a lithographically produced mask if the pattern details are not substantially smaller than a few microns. Electroplating of the dipole material, e.g., gold, can then be performed in those instances wherein a thickness of the deposited dipoles greater than approximately one half of a micron is desired.

According to an example of an embodiment, the dipole array pattern can be formed upon both sides of the substrate. Various types of configurations of the dipole arrays can be formed, as discussed below. The optimum configuration depends on the type of application.

According to an example of an embodiment, generally parallel and substantially identical patterns can be formed upon both sides of the substrate. This configuration enhances the filter's attenuation capability within the band of frequency of design. This configuration can be used when the incident radiation is linearly polarized. Using a quarter wave electronic thickness for the substrate will tend to cancel radiation, e.g., reflections, that are launched from both surfaces of the plate traveling perpendicular to the arrays. As an example, for millimeter waves, e.g., $\lambda=3$ mm to 4 mm, the quarter wave thickness of quartz is approximately 440 microns.

The patterns of the dipole arrays can be configured to produce the desired filter effects at two different frequencies. Thus, each of the two dipole arrays can comprise dipole antennas that have different electrical lengths (and thus different resonant frequencies).

This configuration can be useful when one must filter out two different frequencies simultaneously. This configuration can be used to broaden the frequency band of the filter. This configuration can be used to protect the receiver from the two frequencies of the transmitters in a non-linear radar (NLR) system, as discussed above. It can be used when the incident radiations at both frequencies are linearly polarized and are substantially parallel with respect to one another. If the incident radiations are not substantially parallel with respect to one another, then the two dipole arrays can have different (non-parallel with respect to one another) orientations.

According to an example of an embodiment, dipole patterns of the arrays on the two sides of the substrate can be parallel with respect to one another or can be at an angle, e.g., can be perpendicular, with respect to one another. Non-parallel arrays can be used when the anticipated incident high frequency radiation is randomly, circularly, elliptically, or otherwise non-linearly polarized. Arrays can be stacked, such as to form a three-dimensional filter, to further enhance effectiveness against non-linearly polarized electromagnetic radiation.

The functions and construction of substantially two-dimensional filters are discussed above. The two-dimensional plane of the dipole array can be oriented perpendicular to the incident radiation to enhance the effectiveness of the filtering process. Such use of two-dimensional filters tends to assumed that polarization of the incident radiation is well defined, or at least known, so that it can be readily accommodated.

According to an example of an embodiment, a filter can comprise a three-dimensional structure. Extension of the filter into three dimensions can provide substantially more sophisticated filters, multifunction filters, broadband filters, or filters with comparatively sharp cutoff frequencies.

In accordance with an example of an embodiment, an electromagnetic radiation filter can comprise a plurality of dipole antennas configured to mitigate the transmission of electromagnetic radiation. The transmission of electromagnetic radiation through the filter can be mitigated by scattering the electromagnetic radiation.

The dipole antennas can define one or more arrays of dipole antennas. For example, the dipole antennas can define a two-dimensional or a three-dimensional array thereof.

The dipole antennas can be formed upon one or both sides of a substrate. For example, the dipole antennas are formed upon one or both sides of a quartz substrate.

The dipole antennas can be configured to absorb (and thus subtract from the propagation direction) millimeter wave electromagnetic radiation. The dipole antennas can be configured to absorb electromagnetic radiation other than millimeter wave electromagnetic radiation.

The dipole antennas can be substantially parallel with respect to one another, can be substantially perpendicular with respect to one another, or can be at any desired angle with respect to one another. For example, the dipole antennas can be oriented randomly with respect one to another The dipole antennas can be formed in a three-dimensional array thereof by forming a stack of two-dimensional arrays of dipole antennas. The three-dimensional array can comprise alternating layers of substrates and dipole antennas. The dipole antennas within each layer can have substantially the same dimensions or can have different dimension. The dipole antennas of all of the layers can have substantially the same dimensions or the dipole antennas of each layer can be different with respect to one another (and the dipole antennas within each layer can have substantially the same dimensions or can have different dimensions). Thus, the dipole antennas of at least two different layers can have different dimensions.

As those skilled in the art will appreciate, the dimensions of the dipole antennas determine the resonant frequencies of the electromagnetic radiation at which the induced antenna currents and the transmitted field strength are maximum re-emitted thereby. Thus, the dimensions of the dipole antennas determine the characteristics of the filter defined thereby.

The dipole antennas within each layer can have substantially the same orientation or can have different orientations. The dipole antennas of all of the layers can have substantially the same orientation.

In accordance with an example of an embodiment, an antenna for non-linear radar system can comprise a horn and a filter for inhibiting reception of at least one frequency of electromagnetic radiation by the horn. The filter can comprise plurality of dipole antennas.

In accordance with an example of an embodiment, a non-linear radar system can comprise a transmit antenna configured to transmit first and second frequencies of electromagnetic radiation, a receive antenna configured to receive a third frequency of electromagnetic radiation, and a filter. The filter can be configured to inhibit reception of the first and second frequencies of predetermined portions of the electromagnetic radiation by the receiving antenna.

In accordance with an example of an embodiment, goggles can protect the eyes from electromagnetic radiation. The goggles can comprise a filter. The filter can comprise a plurality of dipole antennas. The dipole antennas can mitigate the transmission of a selected portion of the electromagnetic radiation through the filter.

In accordance with an example of an embodiment, a shield can provide protection from electromagnetic radiation. The shield can comprise a filter that can comprise a plurality of dipole antennas. The dipole antennas can mitigate the transmission of electromagnetic radiation through the filter.

Referring now to FIG. 1, a plan view of an example of an embodiment of a filter 100 is shown. The filter 100 can comprise a quartz substrate 102 and a dipole antenna array 104 disposed upon a planar surface of the substrate 102.

Another dipole antenna array may be disposed on the opposite face of substrate 102. The other dipole antenna array can be identical with respect to the dipole antenna array 104 and can thus have substantially the same frequency response and polarization with respect thereto. Alternatively, the other dipole antenna can be different with respect to the dipole antenna array 104 and can thus have a substantially different frequency response and/or polarization with respect thereto.

According to an example of an embodiment, the filter 100 can be generally rectangular in shape. Alternatively, the filter 100 can be of any other desired shape. For example, the filter 100 can be square, rectangular, triangular, pentagonal, octagonal, round, or oval. Indeed, the filter 100 can have an irregular shape, if desired.

For example, the filter 100 can have an irregular shape in order to fit in various window frames such as those of binoculars, field glasses, or a battle-shield. Such binoculars, field glasses, or battle-shield can be configured so as to provide isolation from flying projectiles while allowing protected viewing through the filter 100.

The substrate 104 can be constructed using quartz that can have a thickness of approximately 440 microns. A two layer dipole array wherein the two layers are separated by only a few micros of an insulator is one example of a configuration. The metal conductive strips defining the dipole elements can be formed using gold (Au).

The filter 100 can have a first edge 110 and an opposite second edge 112 defining a filter width, Dimension A. In a similar manner, the filter 100 can have a third edge 116 and an opposite fourth edge 118 defining a filter height, Dimension B. Dimensions A and B can be sized so as to facilitate use of the filter in a desired application.

Figure 2:
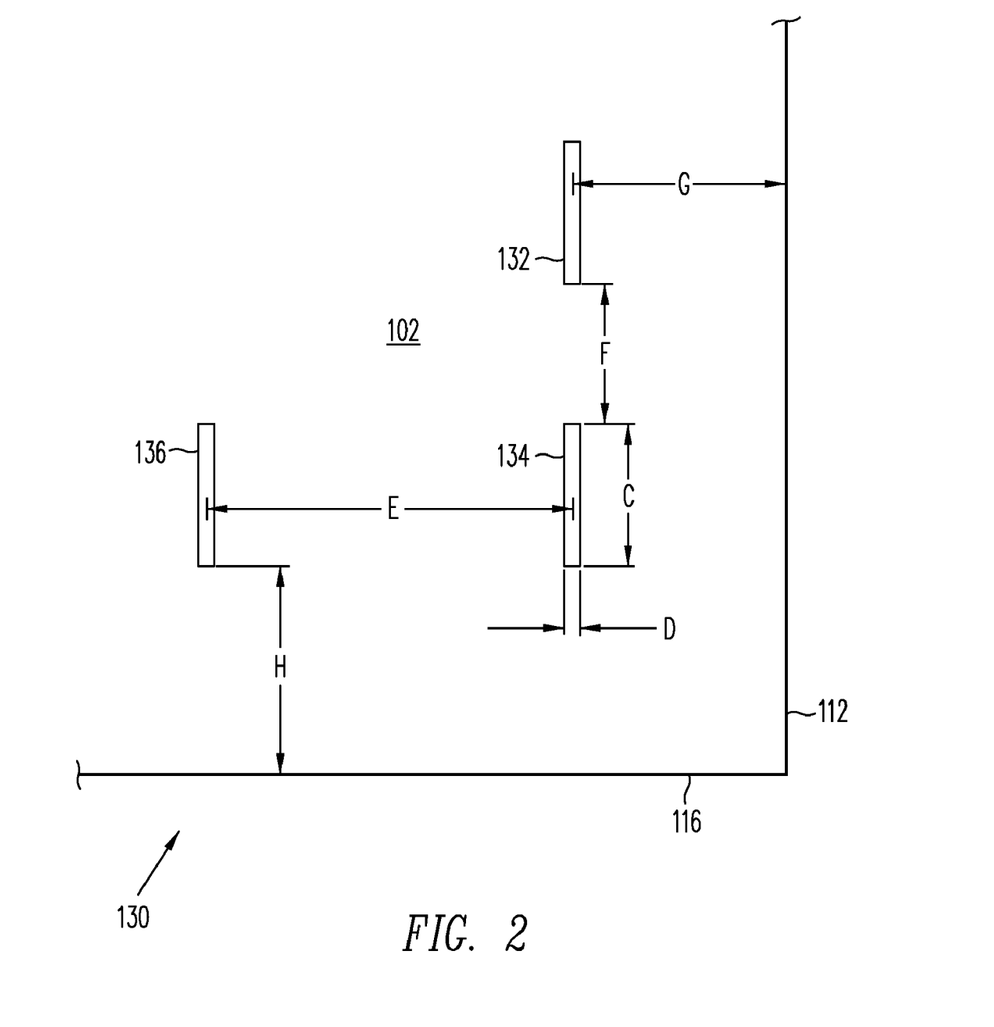
FIG. 2 is a semi-schematic enlarged view of a portion of a filter, such as the circled portion in FIG. 1, according to an example of an embodiment.

Referring now to FIG. 2, a portion of FIG. 1, such as that encircled by dashed lines 2, is shown in greater detail. The dipole antennas of array 104, such as the three examples of dipole antennas 132, 134, and 136 can substantially parallel to one another. The dipole antennas can have any other desired orientation with respect to one another. The dipole antennas can have a random orientation with respect to one another.

The individual dipole length, Dimension C, can be in the range of from approximately 0.5 mm to approximately 2.5 mm, depending upon the desired frequency response. The individual dipole width, Dimension D, can be in the general range of approximately 10 microns to approximately 100 microns. Dimensions C and D can be the same for every dipole within an array or within a plurality of arrays. Dimensions C and D can be different for at least some of the dipoles within an array or within a plurality of arrays.

The horizontal separation between dipoles, Dimension E, can be on the order of approximately 1. The vertical separation between dipoles, Dimension F, can be on the order of approximately 1 mm. These dimensions can be varied depending upon the desired spectral response of the filter. Dimensions E and F can be the same for every dipole within an array or within a plurality of arrays. Dimensions E and F can be different for at least some of the dipoles within an array or within a plurality of arrays. The distances, Dimensions G and H, should not be unnecessarily wide so as to inhibit leakage of radiation around the active part of the filter.

These disclosed dimensions are representative of a selected range in the W-band. Those skilled in the art will appreciate that other dimensions are likewise suitable, particularly for use of the filter in other electromagnetic radiation frequency bands.

Figures 3, 4, 4A:
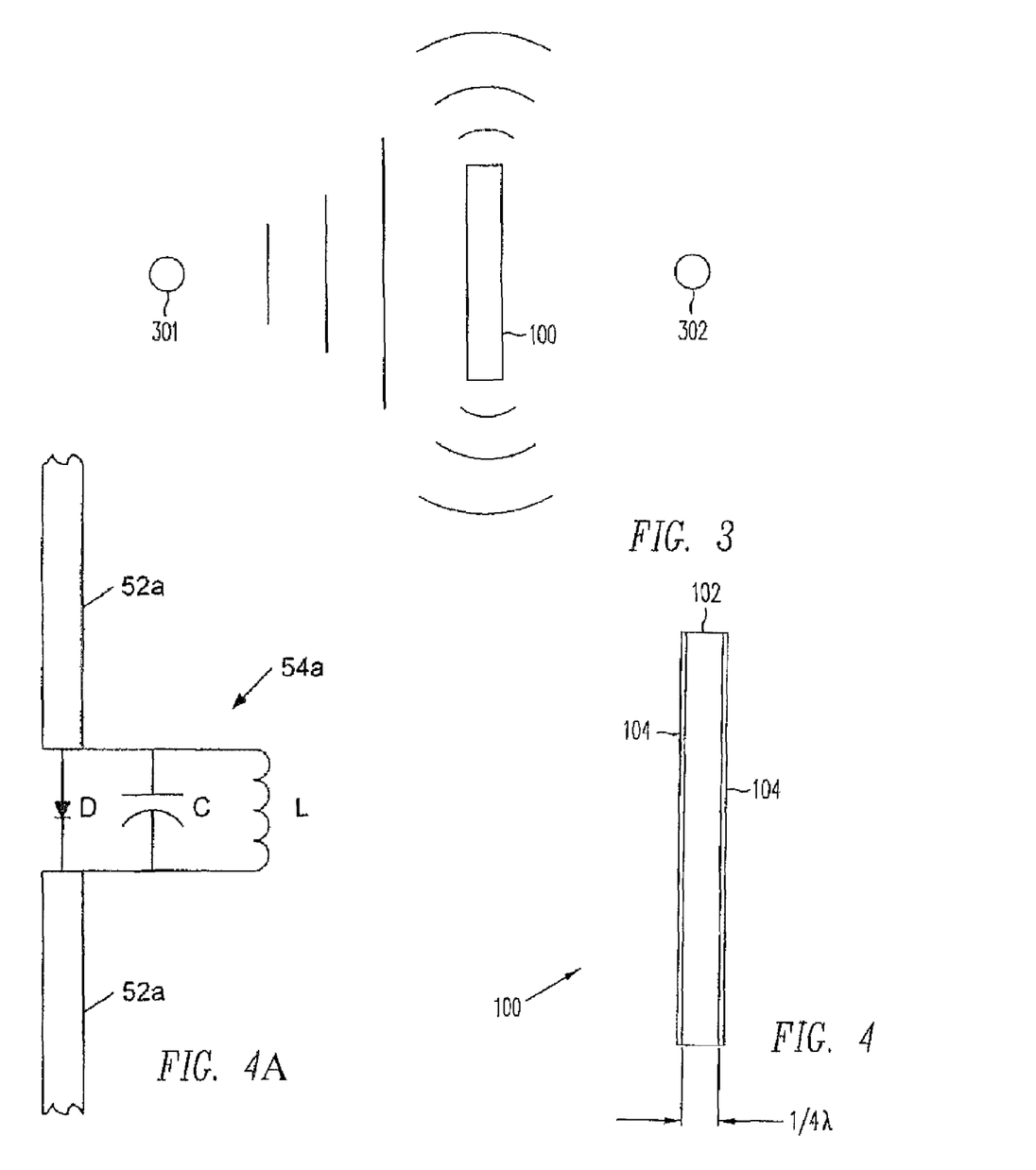
FIG. 3 is a block diagram showing a two-dimensional filter mitigating, e.g., scattering, electromagnetic radiation from a source so as to protect a subject.
FIG. 4 is a semi-schematic side view of a filter having a dipole antenna array formed upon both sides of a substrate, according to an example of an embodiment.
FIG. 4A is a schematic diagram showing details of a dipole antenna according to an example of an embodiment.

Referring now to FIG. 3, a block diagram shows a filter 100 mitigating electromagnetic radiation from a source 301 so as to protect a subject 302. Electromagnetic radiation from the source 301 is blocked by the dipole antenna array 104 of the filter 100 and is re-emitted in a direction that is generally perpendicular to the direction of propagation of the incident electromagnetic radiation coming from the source.

In this manner, the amount of electromagnetic radiation reaching the subject 302, particularly at the resonant frequency of the dipole array, is substantially mitigated. The source 301 is assumed to be far (such that incident radiation from the source has a substantially flat wave front) from the filter and can be any source of electromagnetic radiation for which it is undesirable that at least a portion of the spectrum of the electromagnetic radiation therefrom be incident upon the subject 302. The filter 100 can be one sided, two sided, two-dimensional, or three-dimensional. The filter 100 can be in the form of a sheet, a container, a housing, a package, goggles, a shield, or any other structure. The subject 302 can be a person, an animal, electronic circuitry, part of the front end of a receiver, or anything else.

As shown in FIG. 3, part of the electromagnetic radiation from the source 301 that is to be mitigated or filtered is scattered such that a substantial portion thereof is not incident upon the subject 302. In this manner, the detrimental effects of the electromagnetic radiation upon the subject 302 can be substantially mitigated.

Referring now to FIG. 4, a filter 100 can have a dipole antenna array 104 formed upon both sides of a substrate 102, according to an example of an embodiment. In this manner, two different filters can be formed upon a single substrate to better filter a single frequency and/or polarization of electromagnetic radiation, as discussed above. In this manner, two different filters can be formed upon a single substrate to filter two different frequencies and/or two orthogonal polarizations of the same frequency of electromagnetic radiation, as discussed above.

Figure 5:
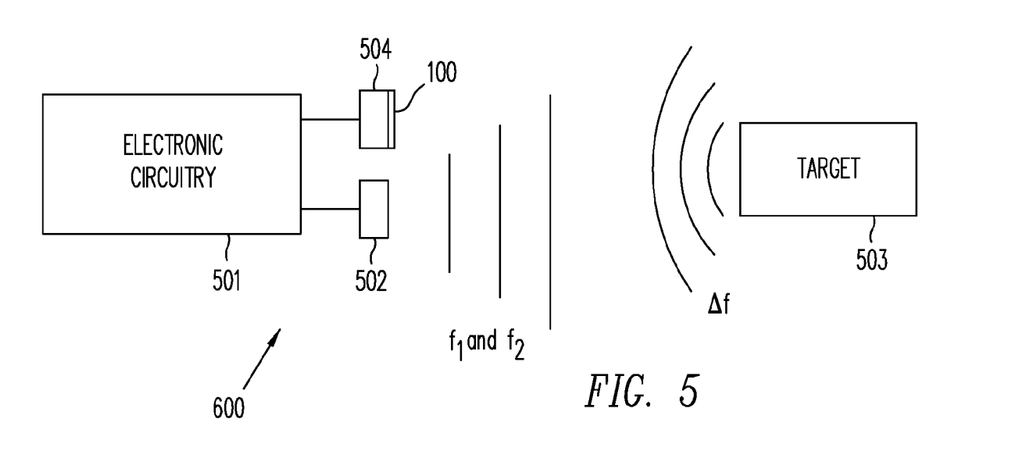
FIG. 5 is a block diagram showing the use of a filter in a non-linear radar (NLR) system, according to an example of an embodiment.

Referring now to FIG. 5, a block diagram shows the use of a filter 100 in a non-linear radar (NLR) system 600, according to an example of an embodiment. A transmit antenna 502 can transmit two frequencies, $f_1$ and $f_2$, to a remote target 503.

Non-linear structures and/or components (including non-linear electronic components such as diodes and transistors) of target 503 can function as a composite dipole antenna that absorbs the two transmitted frequencies $f_1$ and $f_2$, and that re-transmits a difference frequency $\Delta f$ in response to the two incident frequencies.

Examples of composite dipole arrays structures are described in U.S. Pat. No. 6,999,041, entitled Dual Frequency Antennas And Associated Down-Conversion Method, issued Feb. 14, 2006, and in U.S. Pat. No. 7,009,575 entitled High-Frequency Two-Dimensional Antenna and Associated Down-Conversion Method, issued on Mar. 7, 2006, the entire contents of both of which are expressly incorporated herein by reference in their entirety.

A receive antenna 504 receives the difference frequency $\Delta f$, which is then processed by electronic circuitry 501. Such processing can determine the presence of and/or identify the target 503.

However, if the receive antenna 504 receives too much return at the transmitted frequencies, $f_1$ and $f_2$, then $f_1$ and $f_2$ can interact with non-linear components of the electronic circuitry 501 to form an intermodulation product at the difference frequency Δf. Of course, the presence of the difference frequency Δf in the electronic circuitry 501 due to the reception of the transmitted frequencies, $f_1$ and $f_2$, is undesirable. The presence of the difference frequency Δf in the electronic circuitry 501 can mask the presence of the difference frequency Δf return from the target 503 and/or otherwise interfere with the desired operation of the non-linear radar system. This happens because the two Δfs are indistinguishable.

As such, it is desirable to filter the return such that substantially less of $f_1$ and $f_2$ are incident upon the receive antenna 504. According to an example of an embodiment, such filtering can be performed by a dipole array filter 100. The dipole array filter 100 can be positioned such that it substantially mitigates or blocks the reception of $f_1$ and $f_2$ by the receive antenna 504.

Figure 6:
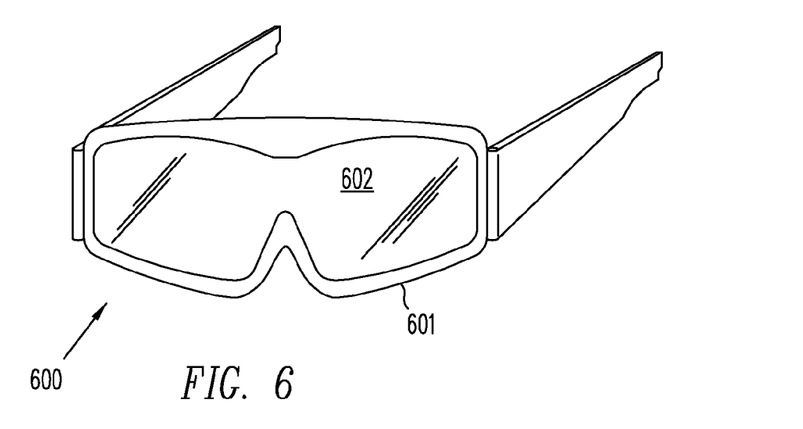
FIG. 6 is a semi-schematic perspective view showing the use of a filter in a pair of goggles, according to an example of an embodiment.
Figure 7:
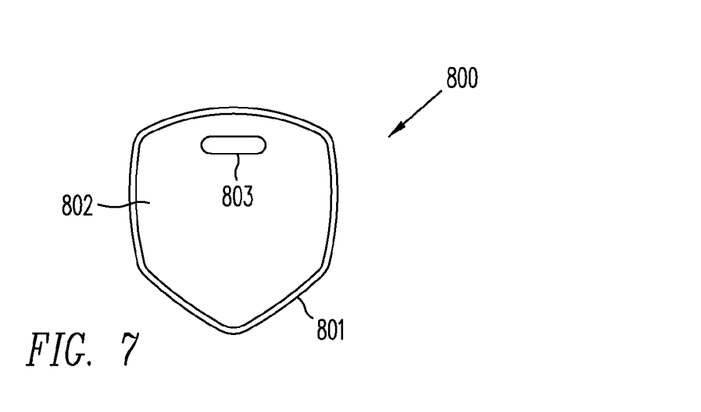
FIG. 7 is a semi-schematic front view of a shield, according to an example of an embodiment.

Referring now to FIGS. 6 and 7, a dipole array filter can be used to protect a person from electromagnetic radiation. Such protection may be beneficial in battlefield situations, for example. In a battlefield situation, electromagnetic radiation can be used as a weapon, such as in an active denial system (ADS). Electromagnetic radiation that is used as a weapon can cause discomfort, disorientation, or otherwise disable a soldier. Thus, it is desirable to mitigate the adverse affect of electromagnetic radiation in such instances. It can also be beneficial to mitigate exposure to electromagnetic radiation in laboratory and industrial environments.

With particular reference to FIG. 6, a pair of goggles 600 can comprise a filter 602, according to an example of an embodiment. The filter 602 can define or be part of a lens or lenses for the goggles 600. A frame 601 can be used to mount the filter 602. Such goggles 600 can protect the eyes from electromagnetic radiation.

The filter 602 can extend in the manner of a face shield so as to provide protection of the eyes, face, head, and/or other parts of the body from electromagnetic radiation. For example, the filter 602 can be configured so as to define or be part of a helmet.

As a further example, filters can be incorporated into standard glasses, such as those intended for everyday use. Such filters can be configured to also attenuate the transmission of visible light (such as visible sunlight) and/or invisible light (such as ultraviolet light from the sun).

With particular reference to FIG. 7, a shield 800 can comprise a filter 802, according to an example of an embodiment. A frame 801 can support and/or protect the filter 802. A window 803 that is transparent to visible light (and that attenuates desired frequencies) can be formed in the shield 800 so as to facilitate protected viewing. Dipoles antennas can be formed upon the entire filter 802, including the window 803. The remainder (non-window) portion of the shield 800 can be transparent, translucent, or opaque.

The non-window portion of the shield can provide more general electromagnetic radiation shielding. Thus, rather than comprising a filter, the non-window portion of the shield can comprise a layer of conductor and/or a conductive mesh that is configured to shield against a very wide band of electromagnetic radiation (rather than against one or more comparatively narrow bands of electromagnetic radiation, as does the filter).

One or more examples of embodiments can be used to protect animals from electromagnetic radiation. For example, the goggles of FIG. 7 and/or the shield of FIG. 8 can be configured for use by animals. For example, such protection can be beneficial for canine use in the battlefield, in Special Weapons and Tactics (SWAT) situations and for police use. As a further example, such protection can be beneficial for equine use by the police in crowd control situations.

It is worthwhile to appreciate that, in some instances, it can be beneficial to protect a user (whether human or otherwise) from friendly (not generated by hostile forces) electromagnetic radiation. For example, in crowd control or riot situations, the police may employ electromagnetic radiation to disperse a crowd. Police officers may be interspersed within the crowd and thus should be protected from this friendly electromagnetic radiation.

According to an example of an embodiment, a filter can be configured to attenuate electromagnetic energy by scattering the electromagnetic energy. Electromagnetic energy within one or more predetermined wavelength band can be scattered. Electromagnetic energy from one or more directions can be scattered.

Generally, the incident electromagnetic radiation will be scattered in a direction that is substantially perpendicular with respect thereto. However, the dipole antennas can be configured so as to scatter the incident electromagnetic radiation in any desired direction.

According to an example of an embodiment, a two-dimensional filter member can comprise a quartz substrate having a first planar surface on a first side of the substrate and a substantially parallel second planar surface on an opposite side of the substrate. The two-dimensional filter member can further comprise a plurality of dipole antennas formed on the first and/or second planar surface of the quartz substrate. The filter can be configured to attenuate electromagnetic energy in a desired frequency range of the electromagnet spectrum passing through the substrate.

The dipole antennas can be disposed on the substrate in an array fashion. Adjacent array elements can be separated from each other based on the wavelength to be attenuated, so as to produce maximum re-radiation of incident electromagnetic radiation along the plane of the substrate and minimum radiation transmitted in a direction perpendicular to the plane.

Dipole antennas can be formed on both the first and second planar surfaces of the quartz substrate such that the first and second arrays are parallel to one another with a substantially similar pattern and are configured to filter substantially the same wavelength; such that the first and second arrays are substantially parallel to one another with a substantially similar pattern and are configured to filter substantially different wavelengths.

The attenuated band of electromagnetic radiation can be in the millimeter (mm) wavelength range. The separation between adjacent dipole antennas can be a first distance comparable to the wavelength of electromagnetic radiation for which attenuation is desired. The length of each dipole can be comparable to one-half the wavelength of electromagnetic radiation for which attenuation is desired. The length of these half-wavelength dipoles can be reduced by an amount determined by the dielectric constant of the material of the substrate that the dipoles are formed upon.

According to an example of an embodiment, the filter can comprise three-dimensional filter. Such a three-dimensional filter member can be configured to function as at least one of a multifunction filter, a broadband filter, and a filter with sharp cutoff frequencies.

According to an example of an embodiment, protective eyewear can comprise at least one filter. The filter can be configured to attenuate by scattering electromagnetic energy in the millimeter (mm) wavelength range.

Such protective eyewear can be worn by humans and/or animals protection against radiation generated by an antipersonnel weapon. For example, such eyewear can be worn to protect against electromagnetic radiation from an Active Denial System. Such eyewear can be configured to provide protection against an anti-personnel weapon that operates in the 94 GHz frequency range.

A single filter can be configured to simultaneously protect both eyes of a human or animal. Alternatively, two filters can be provided, i.e., one for each eye.

According to an example of an embodiment, a shield can have window that comprises a filter. The filter can be configured to attenuate electromagnetic energy by scattering the electromagnetic energy in a predetermined wavelength band. The shield can provide protection from flying projectiles while allowing protected viewing through the filter.

According to an example of an embodiment, a method can comprise receiving electromagnetic energy that is incident upon a first planar surface of a quartz substrate. A plurality of dipole antennas can be disposed upon the first planar surface and arranged in an array so that the separation between adjacent dipole antennas is corrected for the dielectric constant of the substrate and can be approximately equal to the attenuation wavelength and the length of each dipole can be corrected for the dielectric constant of the substrate and can be approximately equal to one-half the attenuation wavelength. The received electromagnetic energy can be re-radiating away from the normal to the plane of the substrate.

The attenuated band of electromagnetic energy can be in the millimeter (mm) wavelength range. The electromagnetic energy can be generated by anti-personnel weapon. The anti-personnel weapon can be configured to operate in the 94 GHz frequency range.

According to an example of an embodiment, a remote electronics detection system can comprise a filter that is configured to attenuate back-reflected (return) frequency components in the received radiation while readily passing a difference frequency produced by detecting the electronics of a target. The remote detection system can comprise, for example, a non-linear radar system.

According to an example of an embodiment, a non-electronic inhibiting apparatus can be configured to inhibit unwanted frequencies from entering a receiver component (such as a receive antenna) of a radar system. According to an example of an embodiment, a passive (non-powered) inhibiting apparatus can be configured to inhibit unwanted frequencies from entering a receiver component (such as a receive antenna) of a radar system.

The receive antenna of such a non-linear radar system can be any desired type of antenna. For example, the receive antenna can be horn antenna, the front end of a receiver waveguide system, a phased array antenna, and/or a dipole or an array thereof.

Any desired combination of two-dimensional and three dimensional filters can be used. For example, a filter assembly can comprise one or more two-dimensional filters that are used in combination to provide one or more three-dimensional filters.

The terms "dipole" and "dipole antenna" can be used interchangeably herein.

Referring to FIG. 4(a), each dipole ante a 52a be joined by a nonlinear resonant circuit 54a comprised of reactive elements including an inductor, L, and a capacitor, C, and a nonlinear element or diode, D. The reactive components can be configured to provide an effective open circuit to beam frequencies, $f_1$ and $f_2$, and a quasi short circuit at the lower (difference) frequency, $\Delta f$. The diode is the nonlinear circuit element that promotes the intermodulation of the two frequencies to their beat frequencies. It will be understood by those of ordinary skill in the art that other resonant circuits or filtering circuits or alternative nonlinear circuit elements may be employed in various forms other than these listed, and are well known in the field of electromagnetic signal processing.

Embodiments described above illustrate but do not limit the invention. It should also be understood that numerous modifications and variations are possible in accordance with the principles of the present invention. Accordingly, the scope of the invention is defined only by the following claims.

We claim:

1. An electromagnetic radiation filter for filtering a difference frequency signal having a frequency $\Delta f$ equaling a difference between a first scattering frequency $f_1$ and a second scattering frequency $f_2$, comprising:
    a dielectric substrate defining a plane; and
    a plurality of dipole antennas arranged in rows on the substrate, wherein each dipole is a one-half wavelength dipole at a frequency between the scattering frequencies $f_1$ and $f_2$, and wherein the dipoles in each row are spaced apart to form an end-fire array at the scattering frequencies such that electromagnetic radiation at the scattering frequencies perpendicularly incident to the substrate is scattered in the plane and wherein the difference frequency signal perpendicularly incident to the substrate passes though the substrate.

2. The electromagnetic radiation filter as recited in claim 1, wherein the dipole antennas are configured to scatter millimeter wave electromagnetic radiation.

3. The electromagnetic radiation filter as recited in claim 1, wherein the dipole antennas are substantially parallel with respect one another.

4. The electromagnetic radiation filter as recited in claim 1, wherein the dipole antennas are formed in a two-dimensional array thereof.

5. The electromagnetic radiation filter as recited in claim 1, wherein the dipole antennas are formed in two-dimensional arrays thereof with one two-dimensional array on each surface of the substrate.

6. The electromagnetic radiation filter as recited in claim 1, wherein the dipole antennas are formed in a three-dimensional array thereof.

7. The electromagnetic radiation filter as recited in claim 1, wherein the dipole antennas are formed in a three-dimensional array thereof, the three-dimensional array comprising a stack of two-dimensional arrays of dipole antennas.

8. The electromagnetic radiation filter as recited in claim 1, wherein the dipole antennas are formed in a three-dimensional array thereof, the three-dimensional array comprising alternating layers of substrates and dipole antennas.

9. The electromagnetic radiation filter as recited in claim 1, wherein the dipole antennas are formed in a three-dimensional array thereof, the three-dimensional array comprising a plurality of layers of dipole antennas, the dipole antennas within each layer having substantially the same dimensions.

10. A method for filtering a difference frequency signal having a frequency $\Delta f$ equaling a difference between a first scattering frequency $f_1$ and a second scattering frequency $f_2$, the method comprising:
    providing a planar dielectric substrate defining a plane that includes a plurality of dipole antennas arranged in rows on the substrate, wherein each dipole is a one-half wavelength dipole at a frequency between the scattering frequencies $f_1$ and $f_2$ and wherein the dipoles in each row are spaced apart to form an end-fire array at the scattering frequencies such that electromagnetic radiation at the scattering frequencies perpendicularly incident to the substrate is scattered in the plane;

receiving electromagnetic radiation at the scattering frequencies perpendicularly to the substrate;

scattering the electromagnetic radiation at the scattering frequencies through the end-fire arrays in the plane defined by the substrate receiving perpendicularly incident difference frequency electromagnetic radiation at the substrate; and passing the incident difference frequency electromagnetic radiation through the substrate.

11. An antenna for non-linear radar system comprising: a horn; and a filter for inhibiting reception of electromagnetic radiation at a scattering frequency $f_1$ and a scattering frequency $f_2$ by the horn, the filter comprising a plurality of dipole antennas arranged in rows on a dielectric substrate defining a plane, wherein each dipole is a one-half wavelength dipole at a frequency between the scattering frequencies, a plurality of non-linear resonant circuits corresponding to the plurality of dipole antennas, and wherein the dipoles in each row are spaced apart to form an end-fire array at the scattering frequencies such that electromagnetic radiation at the scattering frequencies perpendicularly incident to the substrate is scattered in the plane and wherein electromagnetic radiation at a difference frequency equaling a difference between $f_1$ and $f_2$ perpendicularly incident to the substrate passes through the substrate; wherein each of the dipole antennas comprises two antennas that are joined by a nonlinear resonant circuit.

* * * * *